United States Patent
Haldis et al.

(10) Patent No.: US 11,872,146 B2
(45) Date of Patent: Jan. 16, 2024

(54) AORTIC FILTER AND FLOW DIVERTER AND METHODS FOR USE THEREOF

(71) Applicant: SANFORD HEALTH, Sioux Falls, SD (US)

(72) Inventors: Thomas Haldis, Sioux Falls, SD (US); Alexander Drofa, Sioux Falls, SD (US)

(73) Assignee: Sanford Health, Sioux Falls, SD (US)

( * ) Notice: Subject to any disclaimer, the term of this patent is extended or adjusted under 35 U.S.C. 154(b) by 500 days.

(21) Appl. No.: 16/982,701

(22) PCT Filed: Mar. 22, 2019

(86) PCT No.: PCT/US2019/023718
§ 371 (c)(1),
(2) Date: Sep. 21, 2020

(87) PCT Pub. No.: WO2019/183569
PCT Pub. Date: Sep. 26, 2019

(65) Prior Publication Data
US 2021/0007837 A1    Jan. 14, 2021

Related U.S. Application Data

(60) Provisional application No. 62/647,610, filed on Mar. 23, 2018.

(51) Int. Cl.
*A61F 2/90* (2013.01)
*A61F 2/07* (2013.01)
(Continued)

(52) U.S. Cl.
CPC .................. *A61F 2/90* (2013.01); *A61F 2/01* (2013.01); *A61F 2/011* (2020.05); *A61F 2/07* (2013.01);
(Continued)

(58) Field of Classification Search
CPC .. A61F 2/011; A61F 2/07; A61F 2/848; A61F 2/90; A61F 2/01; A61F 2/856;
(Continued)

(56) References Cited

U.S. PATENT DOCUMENTS 8,828,045 B1 *  9/2014  Janardhan ........ A61B 17/12172
606/200
11,000,359 B2 *  5/2021  Torrance .................. A61F 2/958
(Continued)

FOREIGN PATENT DOCUMENTS

| WO | 2006076505 A2 | 7/2006 |
|---|---|---|
| WO | 2017121803 A1 | 7/2017 |
| WO | 2017142874 A2 | 8/2017 |

OTHER PUBLICATIONS

International Search Report for PCT/US2019/023718 dated Aug. 19, 2019, pp. 1-4.

*Primary Examiner* — Sarah A Long
(74) *Attorney, Agent, or Firm* — McDonnell Boehnen Hulbert & Berghoff LLP

(57) ABSTRACT

The disclosure provides example apparatus and methods. One example apparatus includes a first woven stent having a curved form in an expanded state. In the expanded state, at least a first portion of the first woven stent has a weave pattern arranged along an outer curvature of the first woven stent that is different than a weave pattern arranged along an inner curvature of the first woven stent. And the first woven stent is biased toward the curved form due to shape memory.

17 Claims, 13 Drawing Sheets

(51) Int. Cl.
*A61F 2/01* (2006.01)
*A61F 2/848* (2013.01)
(52) U.S. Cl.
CPC ........ *A61F 2/848* (2013.01); *A61F 2002/016* (2013.01); *A61F 2250/0017* (2013.01)
(58) Field of Classification Search
CPC .......... A61F 2002/016; A61F 2002/823; A61F 2250/0017
See application file for complete search history.

(56) References Cited

U.S. PATENT DOCUMENTS

| | | | |
|---|---|---|---|
| 2006/0155359 A1* | 7/2006 | Watson | A61F 2/07 623/1.13 |
| 2015/0157477 A1* | 6/2015 | Shahriari | A61F 2/07 623/1.2 |

* cited by examiner

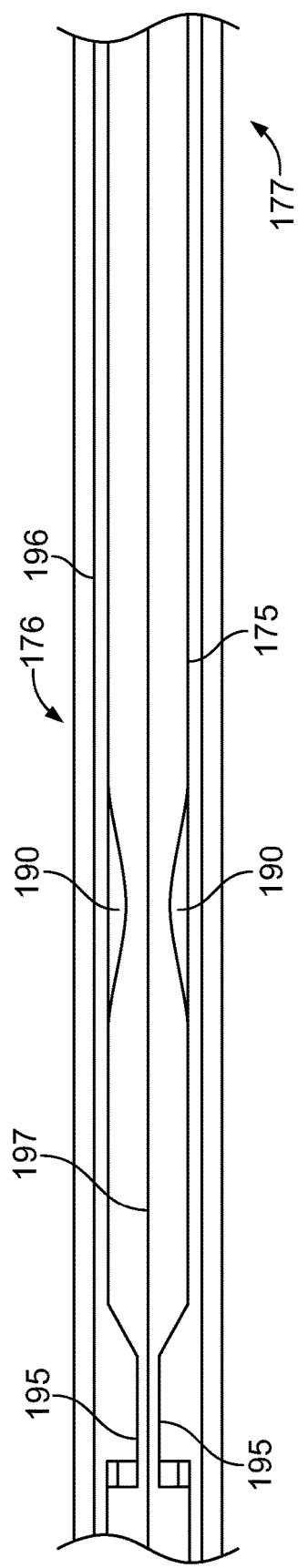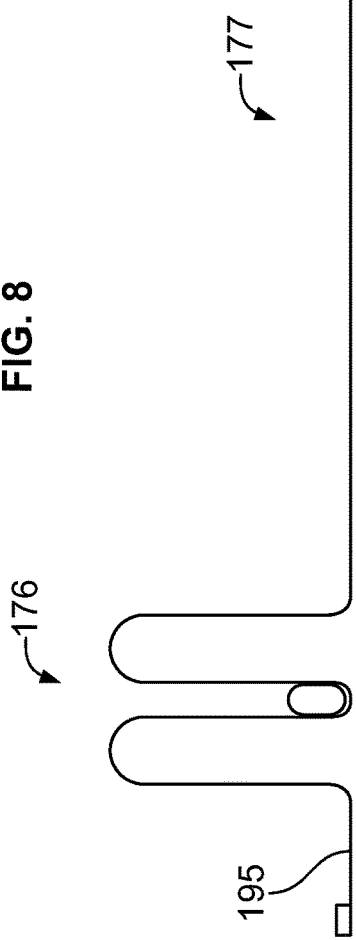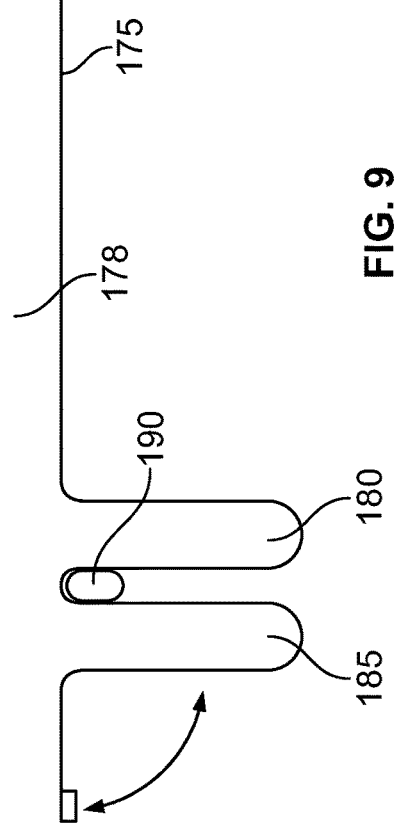

AORTIC FILTER AND FLOW DIVERTER AND METHODS FOR USE THEREOF

CROSS-REFERENCE TO RELATED APPLICATIONS

This application claims the benefit of the filing date of International PCT Patent Application No. PCT/US19/23718, filed on Mar. 22, 2019, that claims priority to Provisional Patent Application No. 62/647,610, filed on Mar. 23, 2018, both of which are hereby incorporated by reference in their entirety.

BACKGROUND

Blood flow to and from the heart is critical in human anatomy. Blood flows from the left ventricle of the heart and travels to the vital organs. Any particulate matter from a diseased aorta or aortic valve during a cardiac procedure could travel to one of these vital organs leading to cell death. In the case of an embolus to the brain, the particulate matter may lead to a stroke. In the case of an embolus to the kidney, the particulate matter may lead to a renal infarct and renal dysfunction. Emboli to any organ may have a similar outcome, though the brain has an increased sensitivity to particulate matter. A patient's aorta may become diseased when (i) there is a build-up of thrombus or atheroma in the aorta, (ii) there is a dissection of the ascending aorta, (iii) the patient has Ehlers-Danlos syndromes ("EDS") or Marfan syndrome ("MFS"), for example, resulting in an enlarged aorta or aortic aneurysm, and/or (iv) the patient has a hostile aortic arch (i.e., "atheroma"). There are additional ways a patient's aorta can be compromised. Currently, when a surgeon advances a device (e.g., a guidewire, catheter, and/or stent) along the aorta to treat conditions of the heart or aortic arch, the device may disturb the thrombus or compromised segment of the aorta, causing an embolus to travel to other parts of the patient's body. This embolus can become lodged in other parts of the patient's body and cause stroke, ischemia of surrounding tissue or in some cases, death.

SUMMARY

In a first aspect, an example apparatus is disclosed. The apparatus includes a first woven stent having a curved form in an expanded state. In the expanded state, at least a first portion of the first woven stent has a weave pattern arranged along an outer curvature of the first woven stent that is different than a weave pattern arranged along an inner curvature of the first woven stent. And the first woven stent is biased toward the curved form due to shape memory.

In a second aspect, an example apparatus is disclosed. The apparatus includes (a) a woven stent and (b) a filter removably coupled to an internal sidewall of the woven stent. The filter has a plurality of anchors arranged around a periphery of the filter and the woven stent has a plurality of attachment points arranged to correspond to the plurality of anchors such that the filter is mechanically or electrolytically coupled to the woven stent.

In a third aspect, an example method is disclosed. The method includes (a) delivering the apparatus according to the first aspect to either to an aortic arch via a catheter, (b) advancing a first end of the first woven stent out of the catheter and deploying the first end to a location at or between an aortic valve and a brachiocephalic artery, and (c) advancing a second end of the first woven stent out of the catheter and deploying the second end at a location distal to a left subclavian artery.

In a fourth aspect, an example method is disclosed. The method includes (a) delivering the apparatus according to the second aspect to an aortic arch via a catheter, where the apparatus comprises a filter removably coupled to the woven stent, the filter having an elongated wire coupled to a second end of the filter, (b) advancing a first end of the woven stent out of the catheter and deploying the first end to a location at or between an aortic valve and a brachiocephalic artery; and (c) advancing a second end of the woven stent out of the catheter and deploying the second end at a location distal to a left subclavian artery.

The features, functions, and advantages that have been discussed can be achieved independently in various examples or may be combined in yet other examples, further details of which can be seen with reference to the following description and drawings.

BRIEF DESCRIPTION OF THE DRAWINGS

FIG. 8 is a diagrammatic representation of a cross-sectional side view of a second woven stent, according to one example implementation, disposed in a catheter in a compressed state;

FIG. 9 is a diagrammatic representation of a cross-sectional side view of the second woven stent, according to the example of FIG. 8, in an unconstrained expanded state;

Figure 1:
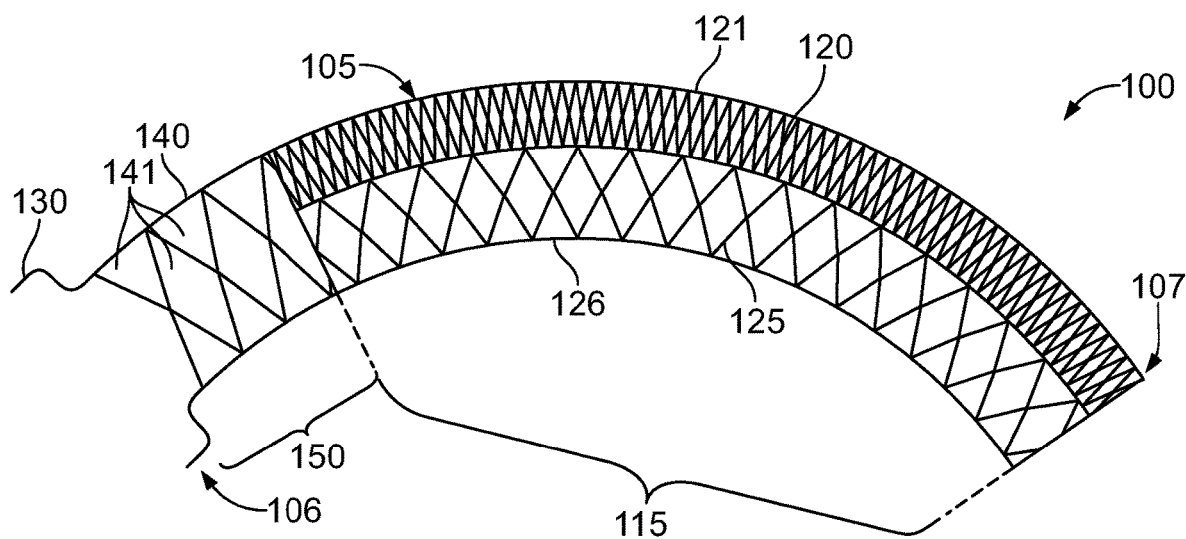
FIG. 1 is a diagrammatic representation of a side view of an apparatus, according to one example implementation.
Figure 2:
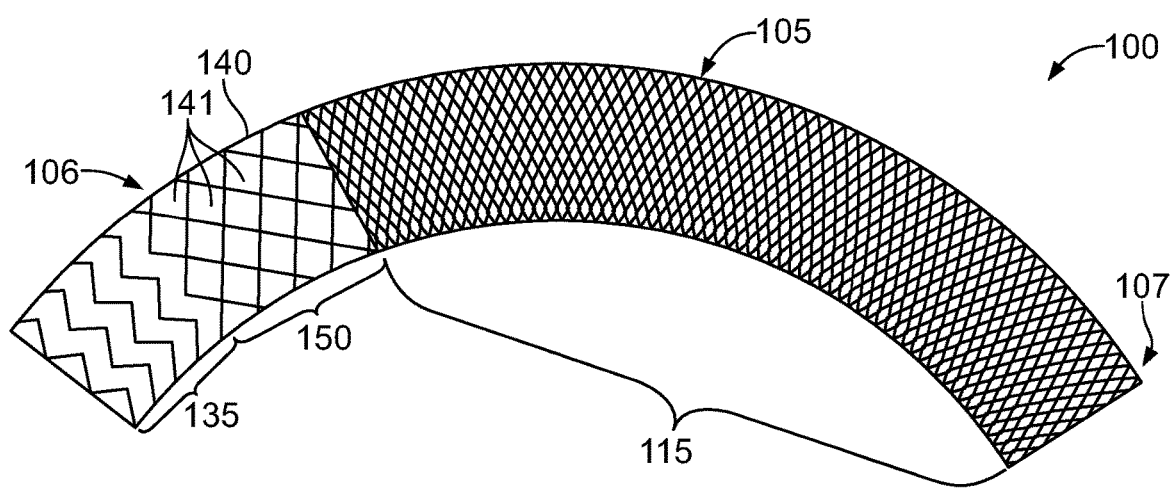
FIG. 2 is a diagrammatic representation of a side view of an apparatus, according to one example implementation.
Figure 3:
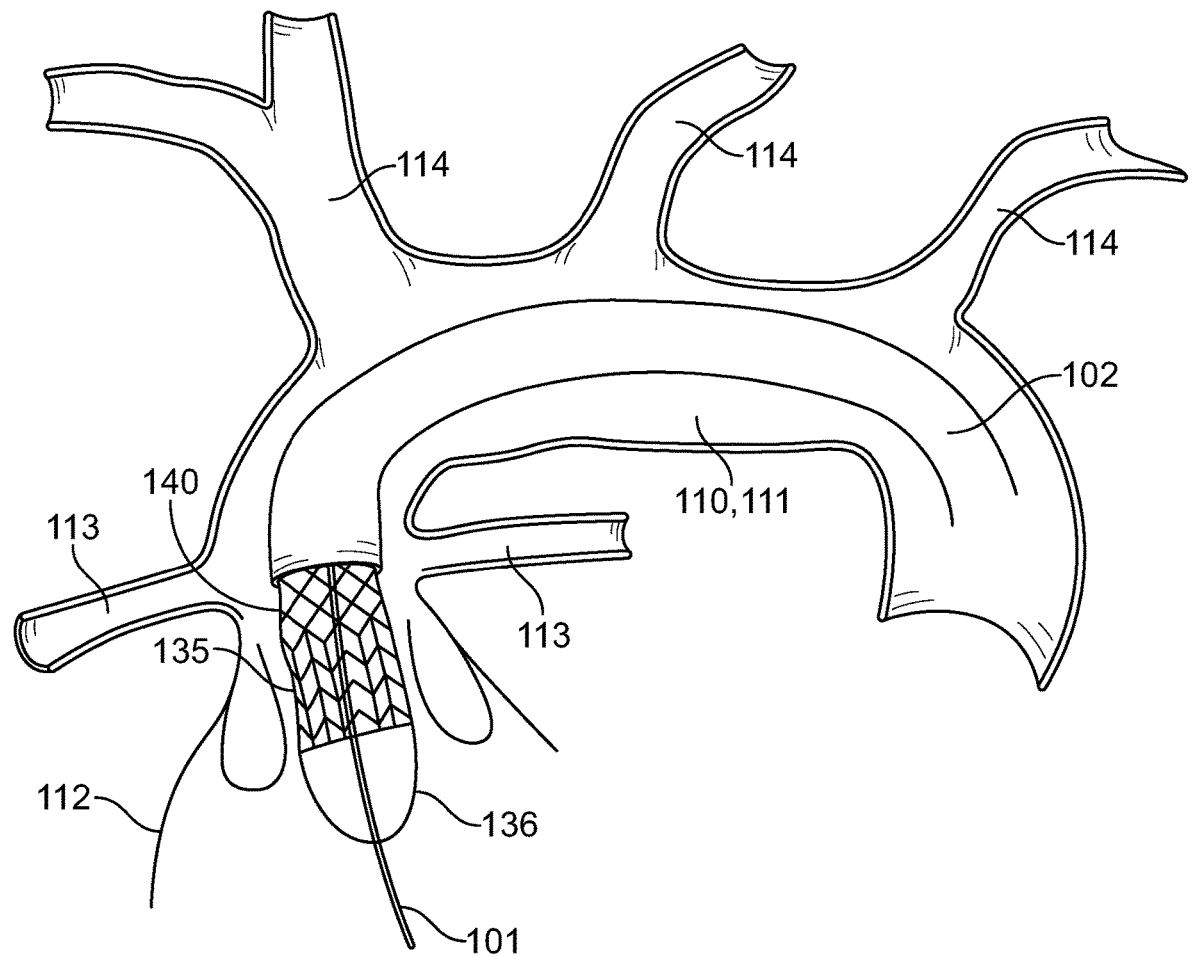
FIG. 3 is a diagrammatic representation of a side view of the apparatus, according to the example of FIG. 2, in a partially deployed position.
Figure 4:
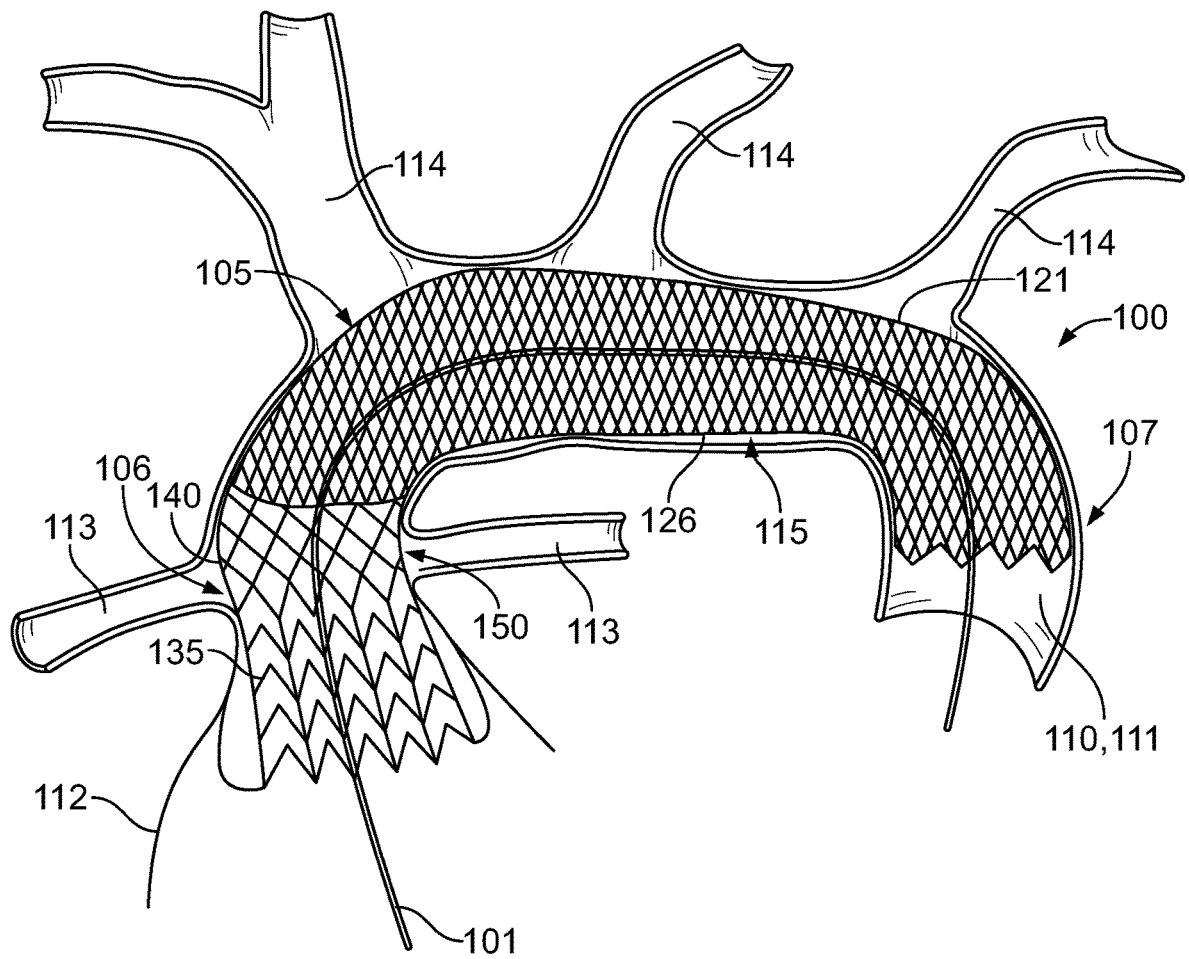
FIG. 4 is a diagrammatic representation of a side view of the apparatus, according to the example of FIG. 2, in a fully deployed position.
Figure 5:
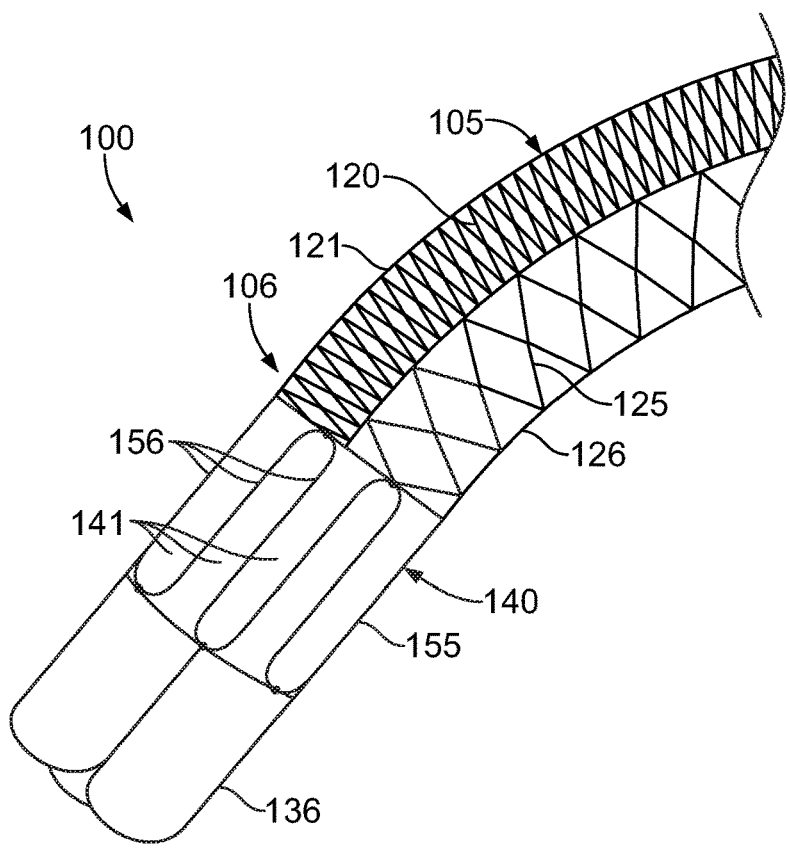
FIG. 5 is a diagrammatic representation of a partial side view of the apparatus, according to one example implementation.
Figure 6:
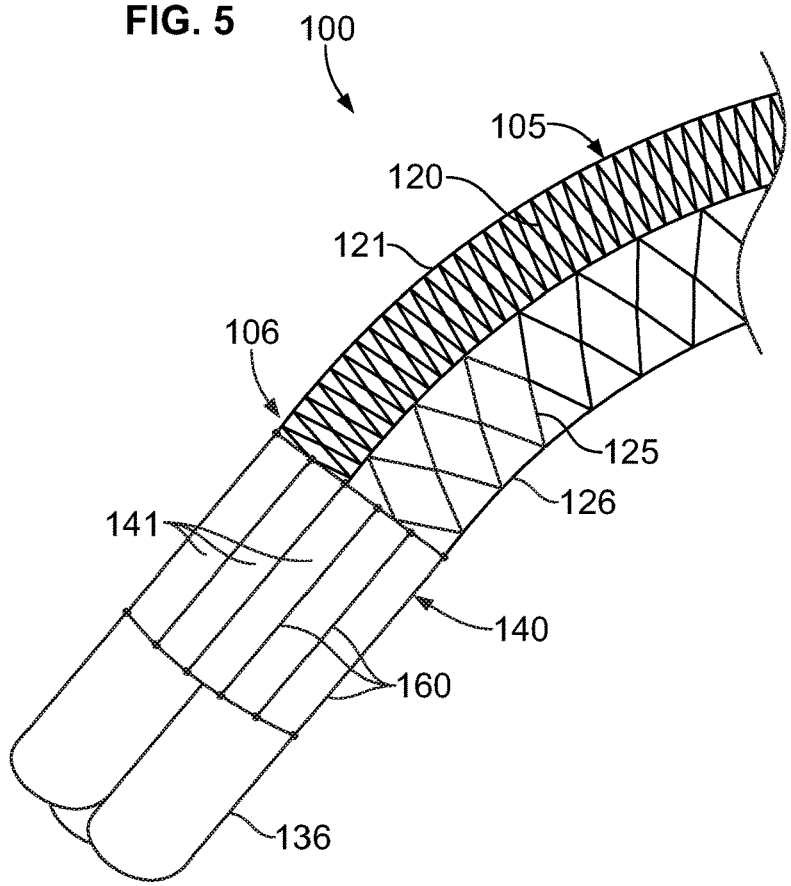
FIG. 6 is a diagrammatic representation of a partial side view of the apparatus, according to one example implementation.

The drawings are for the purpose of illustrating examples, but it is understood that the inventions are not limited to the arrangements and instrumentalities shown in the drawings.

DETAILED DESCRIPTION

As used herein, with respect to measurements, "about" means +/−5%.

As used herein, a "catheter" is an apparatus that is connected to a deployment mechanism and is configured to house a medical device that can be delivered over a guidewire, for example. The catheter may include a guidewire lumen for over-the-wire guidance and may be used for delivering the medical device to a target lumen or for retraction of a filter.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, a "woven stent" is typically a cylindrical frame and means any device or structure that adds rigidity and/or expansion force to a native or prosthetic vessel, valve, or artery. The woven stent can be made of any suitable mesh material, including but not limited to biocompatible metals, implantable quality stainless steel wires, nitinol, cobalt, magnesium, nickel, titanium and alloys thereof, and biocompatible plastics.

As used herein, "shape memory" means any structure that has an original shape that can be deformed or molded into another shape, but returns to the original shape under certain circumstances (e.g., removal of force, temperature, pressure, etc.).

As used herein, a "flow diverter" means any device that disrupts blood flow into an aneurysmal sac to permit a slow leak into the sac to generate thrombus and effectively seal the aneurysm, while permitting normal channels of blood flow to continue and regenerate.

As used herein, "lumen" refers to a passage within an arterial or tubular structure, such as the pulmonary arteries or a passage within the tubular housings or catheters through which the guidewire may be disposed.

As used herein, "first end" refers to a distal end of the device or component thereof, and "second end" refers to a proximal end of the device or component thereof.

As used herein, "distal" with respect to a portion of the apparatus means the end of the device (when in use) nearer the treatment zone (e.g., the pulmonary artery) of the subject and the term "proximal" means the portion of the device (when in use) further away from the targeted lumen of the subject and nearer the access site and the operator.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Exemplary apparatus and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

The apparatus and methods disclosed herein are contemplated for safely and effectively treating compromised aortas, including but not limited to, aortic valves and arches, by providing a pipeline of woven stent apparatuses that pin back any existing thrombus and aneurysms, thereby allowing a surgeon to safely advance devices through the aorta.

The apparatus and methods for use thereof may be beneficially arranged to maintain blood flow to the coronary arteries and Great vessels, improving perfusion and preventing emboli from traveling through the Great vessels. The apparatus and methods may also advantageously act as a flow diverter, reducing the rate and pressure of blood flow into an aneurysmal sac thereby permitting thrombus to fill the aneurysmal sac and promote regeneration of blood flow pathways. The differential weave arranged along the outer curvature of the woven stent relative to the weave pattern arranged along the inner curvature of the woven stent permits the pick density of the inner curvature to be equal to or greater than the pick density of the outer curvature such that the differential weave acts as a flow diverter. The differential weave pattern has the benefit of jailing the atheroma thereby preventing embolization. In various other embodiments, Gore-Tex or PTFE graft may cover one more segments of the woven stent.

Thus, in a first aspect shown in FIGS. 1-6, an apparatus 100 is described that includes a first woven stent 105 having a curved form in an expanded state, for example, when the apparatus 100 is delivered over a guidewire 101 and deployed from a catheter 102 in a target lumen 110, for example the aorta 111. In the expanded state, at least a first portion 115 of the first woven stent 105 has a weave pattern 120 arranged along an outer curvature 121 of the first woven stent 105 that is different than a weave pattern 125 arranged along an inner curvature 126 of the first woven stent 105. The first woven stent 105 is biased toward the curved form due to shape memory. In one example, the first woven stent 105 is configured to act as a flow diverter. This arrangement may beneficially disrupt blood flow into an aneurysmal sac, only permitting a slow leak of blood into the sac, generating thrombus and sealing the aneurysm. This arrangement may further permit normal channels of blood flow to continue through the aorta 111. In one example, a diameter of the first woven stent 105 ranges from about 5 mm to about 60 mm in the expanded state, and a length of the first woven stent 105 ranges from about 10 mm to about 1000 mm in the expanded state.

In some examples, in the expanded state, a first end 106 of the first woven stent 105 tapers outwardly in the form of a flange 130, shown in FIG. 1. This feature may have the technical effect of allowing the first woven stent 105 to mate with the sinotubular junction 112 so as to anchor the first woven stent 105 within the aorta 111 to prevent a shift of the apparatus 100 downstream. This feature may be beneficial in treating a patient's hostile arch (i.e., "atheroma") that starts at the sinotubular junction 112. By mating with the sinotubular junction 112, the first woven stent 105 permits healthy tissue-to-healthy tissue anchoring for treatment of segments of the aorta 111.

In alternative examples, an anchoring stent 135 or a prosthetic valve 136 may be coupled to a first end 106 of the first woven stent 105 such that there is a flow window 140 having a plurality of openings 141 arranged therebetween to permit blood flow through the plurality of openings 141. In one optional embodiment, the flow window 140 has a length ranging from 4 mm to 20 mm in the expanded state. In one example, the plurality of openings 141 of the flow window 140 may be defined in a second portion 145 of the first woven stent 105 arranged at the first end 106 of the first woven stent 105. The flow window 140 has the technical effect of permitting blood to flow through to the coronary arteries, whereas the first portion 115 of the first woven stent 105 is arranged to divert and/or slow blood flow, reducing pressure on the vessel walls, permitting thrombus to fill the aneurysmal sac and blood pathways to regenerate. A pick density of the second portion 150 of the first woven stent 105 is lower than a pick density of the first portion 115 of the first woven stent. For example, the pick density of the first portion 115 of the first woven stent 105 has a pore size ranging from 0.005 mm$^2$ to 1.0 mm$^2$ in the expanded state, and the pick density of the second portion 150 of the first woven stent 105 has a pore size ranging from 0.01 mm$^2$ to 1.0 mm$^2$ in the expanded state. Porosity may range from 5 to 95 percent of the surface area of the first woven stent 105 depending on the deployment configuration. For example, the first woven stent 105 may provide "custom" flow diversion depending on whether and the degree to which the first woven stent 105 is "packed." The pick density (or pore size) is selected to provide adequate filtration, protect the aortic arch from hemodynamic forces, and permit adequate perfusion to the aneurysmal sac, for example. In various examples, a lace trellis stitch, a waterfall stitch or a three-step stitch may be utilized to provide a less dense weave.

In additional examples, the flow window 140 may include a radial stent 155 (FIG. 5) formed from a sinusoidal-shaped wire or a plurality of radially spaced-apart supports 160 (FIG. 6) that couple the anchoring stent 135 or the prosthetic valve 136 to the first woven stent 105. The plurality of openings 141 of the flow window 140 are defined between sinusoidal components 156 of the radial stent 155 or the plurality of radially spaced-apart supports 160. The plurality of openings 141 are sized and arranged to minimize any interruption of blood flow to the coronary arteries 113.

Figure 7:
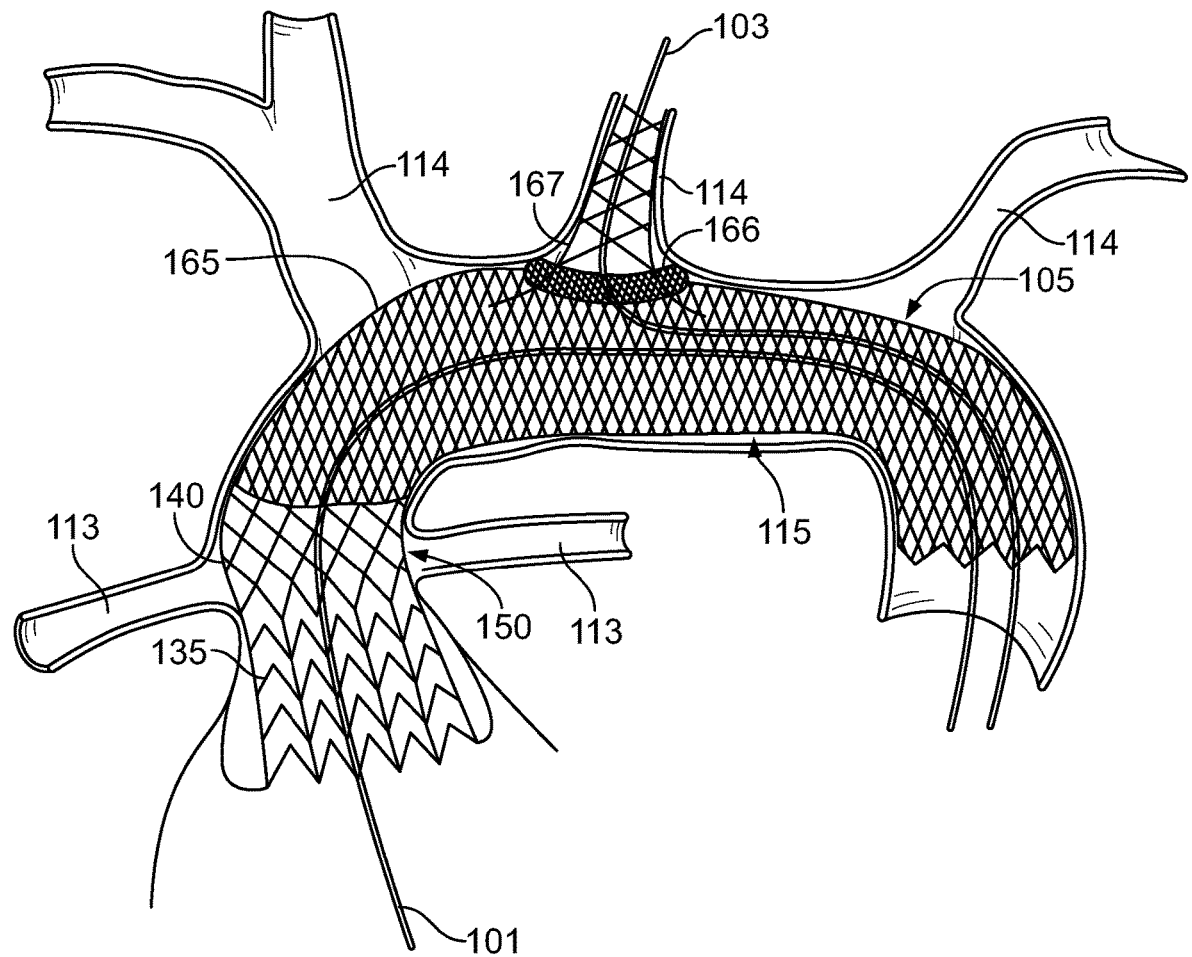
FIG. 7 is a diagrammatic representation of a side view of an apparatus, according to one example implementation.

In one example shown in FIG. 7, a sidewall 165 of the first woven stent 105 is configured to be penetrated by a guidewire 103 or catheter and thereby cause a punctured portion 166 of the first woven stent 105 to roll backwards forming a cuff around the guidewire 103 or the catheter. This configuration beneficially permits additional stent grafts 167 to be deployed that extend into one or more of the Great vessels 114 to exclude the aneurysm. For example, the punctured portion 166 could be a circular or a semicircular section that includes cobalt chromium or stainless steel, for example, configured to be balloon expandable and incorporated into the self-expanding stent.

In some examples, the plurality of openings 141 of the flow window 140 are configured to be expanded and deformed upon application of force from an expandable balloon, catheter or guidewire. In some examples, the weave pattern 120 arranged along the outer curvature 121 of the first woven stent 105 is configured to prevent the passage therethrough of particles having a diameter of about 20 μm or greater. This configuration may beneficially prevent emboli from advancing through the Great vessels 114.

In a further example, shown in FIGS. 8-11, the apparatus 100 includes a second woven stent 175 configured to transition between a compressed state (FIG. 8) and an expanded state (FIG. 9). In the compressed state, the second woven stent 175 has an elongate tubular form contained in a catheter 196. In the expanded state, the second woven stent 175 forms a first retention disk 180 and a second retention disk 185 arranged in series at a first end 176 and a tubular form at a second end 177 such that a lumen 178 is defined between the first end 176 and the second end 177 of the second woven stent 175. The second woven stent 175 is configured to be disposed through one of the plurality of openings 141 of the flow window 140 in the expanded state and arranged such that (i) a portion of the first end 106 of the first woven stent 105, (ii) a radial stent structure 155 or (iii) two radial spaced-apart supports 160 of the flow window 140 are arranged between the first retention disk 180 and the second retention disk 185. And the second end 177 of the second woven stent 175 is configured to be disposed within a coronary artery 113. The lumen 178 of the second woven stent 175 permits blood flow to be maintained to the coronary arteries, renal arteries, subclavian artery, carotid arteries, innominate artery, iliac arteries or mesenteric artery. The second woven stent 175 may be made of nitinol, stainless steel, cobalt chromium or combinations thereof. In addition, the second woven stent 175 may be coupled to a graft or coated with a drug. In one optional example, the lumen 178 has a diameter ranging from 2 mm to 50 mm. In another optional example, the tubular form at the second end 177 of the second woven stent 175 has a length ranging from 6 mm to 500 mm. In a further optional example, the first retention disk 180 and the second retention disk 185 may extend radially from the exterior of the lumen 178 a distance ranging from 5 mm to 20 mm.

In an alternative embodiment, the first woven stent 105 may be punctured via a catheter or guidewire or may have pre-existing fenestrations in the sidewall of the first woven stent 105. In still further optional embodiments, the second woven stent 175 is configured to be disposed through any previously-placed stent graft or woven stent that is configured to be penetrated by a guidewire or catheter or that has a fenestration in the expanded state, and a wall of such stent graft or woven stent is arranged between the first retention disk 180 and the second retention disk 185 such that the second end 177 of the second woven stent 175 is configured to be disposed within a coronary artery 113.

In another embodiment, shown in FIGS. 8-9, Gore-Tex, felt, gel-foam or combinations thereof 190 be coupled to the exterior 179 of the second woven stent 175 between the first retention disk 180 and the second retention disk 185 to thereby increase efficacy of the seal.

In a further embodiment, the second woven stent 175 includes a plurality of detachment tabs configured 195 to be removably coupled to a catheter 196 in the compressed state, as shown in FIGS. 8-9. The detachment tabs 195 have shape memory and are configured to lie flat against the first end 176 of the second woven stent 175 in the expanded state. The detachment tabs 195 permit retrieval and repositioning of the second woven stent 175 during deployment. Once the second woven stent 175 is deployed, the detachment tabs 195 may be detached from the delivery device by way of electrolytic detachment or mechanical detachment. Mechanical detachment may include rotating a knob coupled to frame loops via the catheter 196 to detach from the tabs or may include engaging tabs having shape memory within a catheter 196 that fold against the first retention disk 180 upon release from the catheter 196, as shown in FIG. 9.

Figure 10:
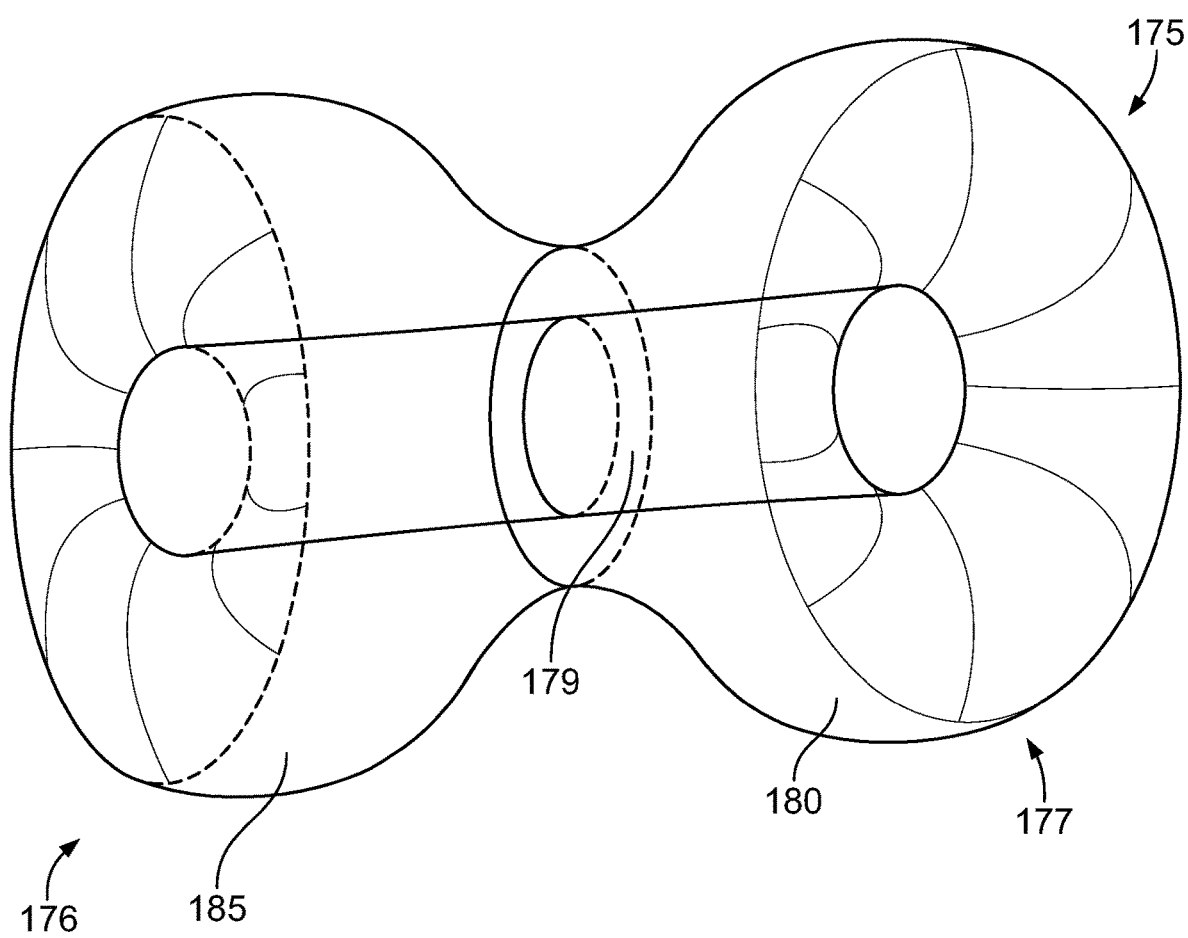
FIG. 10 is a diagrammatic representation of a perspective side view of an apparatus, according to one example implementation.

In another embodiment, shown in FIG. 10, the second woven stent 175 has a first retention disk 180 at a second end 177 and a second retention disk 180 at a first end 176 in the expanded state such that a lumen 178 is defined between the first end 176 and the second end 177 of the second woven stent 175. In this embodiment, there is no tubular form arranged at the second end 177. In this embodiment, the second woven stent 175 is configured to be disposed through a native valve such that the native valve is arranged between the first retention disk 180 and the second retention disk 185 thereby permitting blood to flow through the lumen 178 of the second woven stent 175. In this arrangement, the first retention disk 180 and the second retention disk 185 are toroidal in shape.

Figure 11:
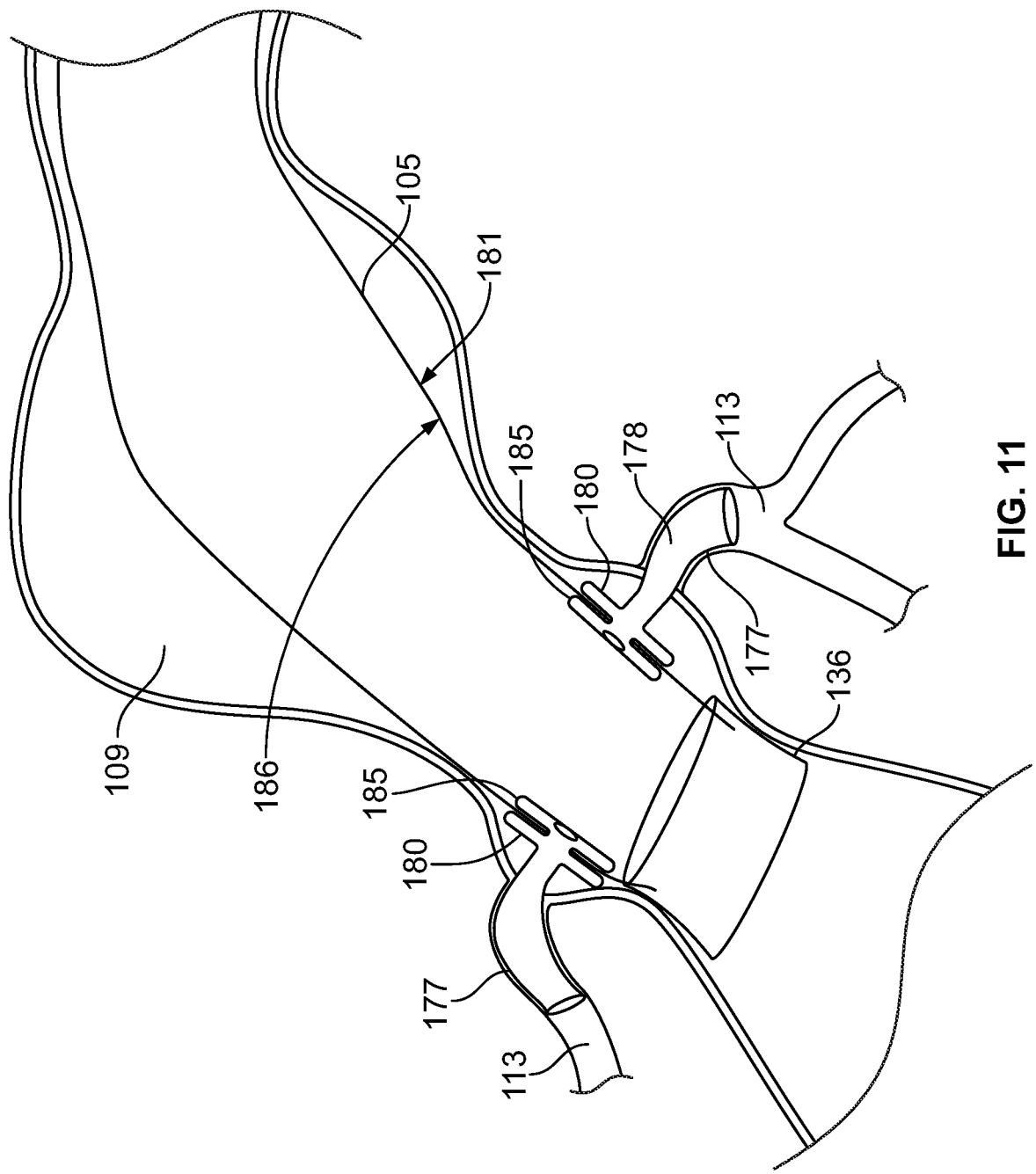
FIG. 11 is a diagrammatic representation of a side view of an apparatus, according to one example implementation, in a deployed position.
Figure 12:
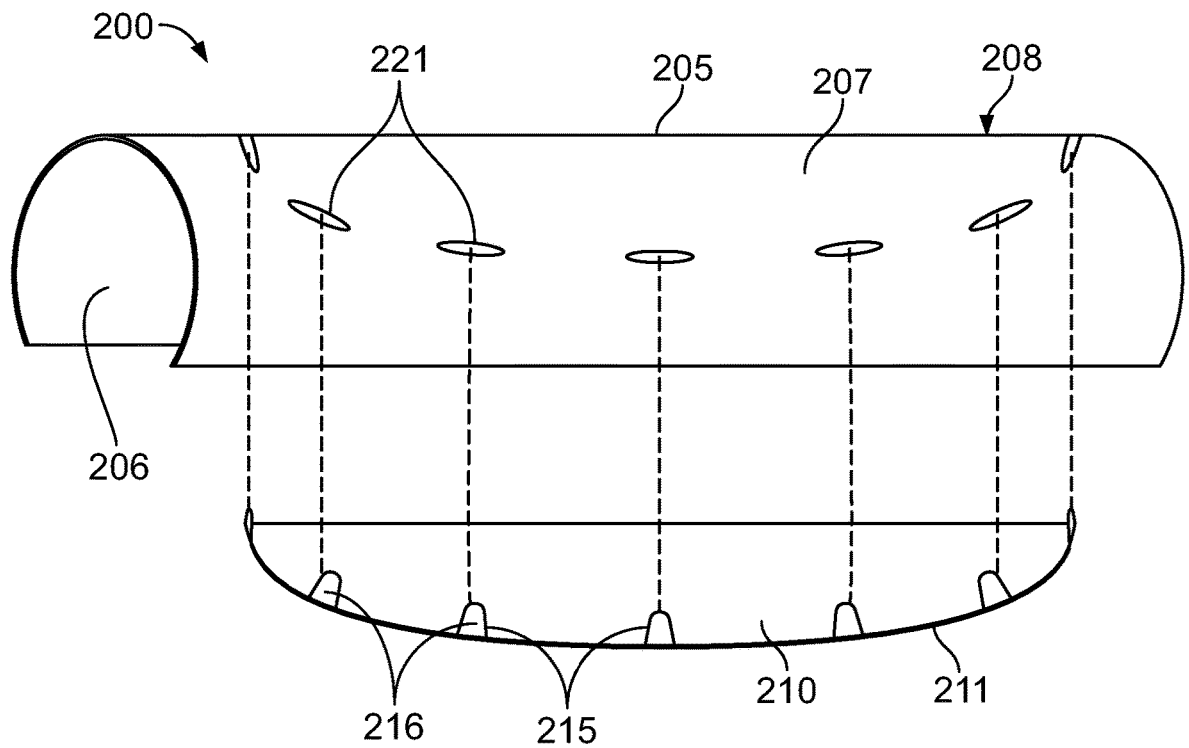
FIG. 12 is a diagrammatic representation of a partial side view of an apparatus, according to one example implementation, prior to coupling the woven stent and the filter together.

In operation, as shown in FIG. 11, the first woven stent 105 is deployed across an aneurysm 109 and engaged with a catheter and a guide wire 197 is disposed within the coronary artery 113. An intermediate catheter 196 may be disposed over the guide wire 197 and is advanced into the coronary artery 113. The second woven stent 175 may be self-expanding and delivered through the intermediate catheter 196, such that the intermediate catheter 196 is slowly withdrawn outside the native coronary ostium. The first retention disk 180 is deployed on the outer surface 181 of the woven stent 105 or stent graft. Then the second retention disk 185 is deployed on the inner luminal aspect 186 of the woven stent 105, such as the first woven stent 105 and/or flow window 140, a stent graft or a valve.

In an alternative embodiment, the first retention disk 180 and the second retention disk 185 at the first end 176 of the second woven stent 175 may be made of nitinol and the tubular form at the second end 177 of the second woven stent 175 may be cobalt chromium and balloon-mounted. A plurality of welds may couple the cobalt chromium balloon-mounted stent and the nitinol stent together. In operation, a guide wire 197 may be disposed in the coronary artery 113. The second woven stent 175 may then be advanced over the guide wire 197 and the balloon may be inflated to deploy the second end 177 of the second woven stent 175 in the coronary artery 113. The technical effect of such an arrangement is to provide a distal anchor for the controlled unsheathing of the nitinol portion of first retention disk 180 and the second retention disk 185 as discussed above. This deployment of the first woven stent 105 and the second woven 175 stent thereby seals the endoleak.

In a second aspect of the disclosure, shown in FIGS. 12-16, the apparatus 200 includes a woven stent 205 and a filter 210 removably coupled to an internal surface 206 of sidewall 207 of the woven stent 205. The filter 210 has a plurality of anchors 215 arranged around a periphery 211 of the filter 210 and the woven stent 205 has a plurality of attachment points 220 arranged to correspond to the plurality of anchors 215 such that the filter 210 is mechanically or electrolytically coupled to the woven stent 205. In one example, the filter 210 may have a pore size ranging from 20 μm to 100 μm to thereby obstruct flow of particulate matter into cerebral circulation, for example. In another example, the filter 210 may have a pick density ranging from 0.001 mm to 1.0 mm to permit passage of a catheter, guidewire, and/or stent.

The filter 210 has the technical effect of permitting blood flow to the Great vessels 114 while preventing emboli from advancing to the brain. Upon completion of the stent placement procedure, the filter 210 may be removed thereby permitting normal blood flow to resume. The filter 210 may be removed immediately after placement of the woven stent 205 up to two days later depending up the degree of thrombus present in the aortic arch. The technical effect of the removable filter 210 is to remove any particulate to avoid jailing the Great vessels 114 that could lead to ischemic symptoms. In another embodiment, the filter 210 may remain in place indefinitely.

Figure 13:
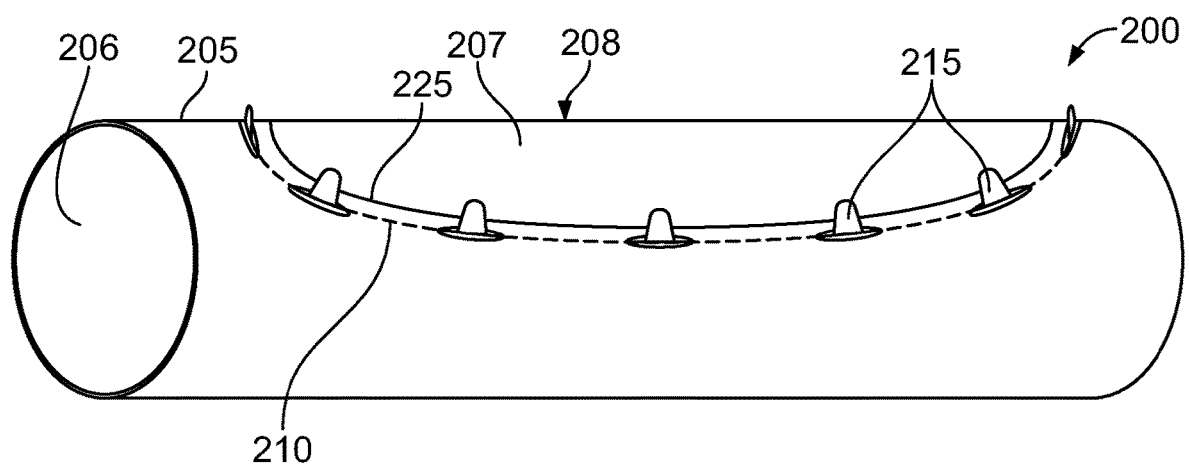
FIG. 13 is a diagrammatic representation of a side view of an apparatus, according to one example implementation, after the woven stent and the filter are coupled together.
Figure 14:
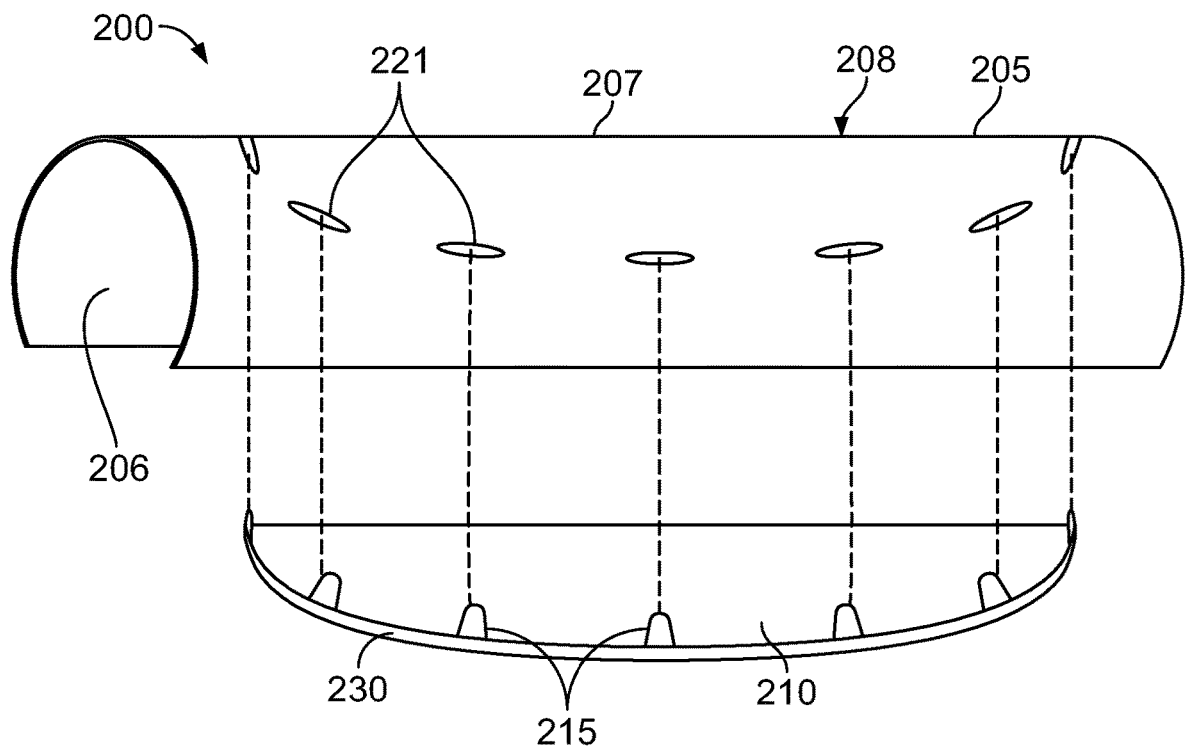
FIG. 14 is a diagrammatic representation of a partial side view of an apparatus, according to one example implementation, prior to coupling the woven stent and the filter together.

In one example, shown in FIGS. 13-14, the plurality of attachment points 220 include a plurality of slits 221 arranged in a sidewall of the woven stent 205, and the plurality of anchors 215 extend perpendicular to the filter and are disposed through the plurality of slits 221 of the woven stent 205 for removable coupling to the woven stent 205. In a further example, a plurality of openings 216 are defined in the plurality of anchors 215 and the plurality of anchors 215 have shape memory biased to maintain the plurality of anchors 215 perpendicular to the filter 210, and where the plurality of anchors 215 are configured to collapse against an exterior 208 of the woven stent 205 in the expanded state in response to an external force. This arrangement permits a bio-compatible string 225 to be disposed through the plurality of openings 216 defined in the plurality of anchors 215. In various embodiments, the bio-compatible string 225 may be polypropylene suture, catgut, nylon, PVDF, stainless steel, poliglecaprone and polydioxanone sutures. The bio-compatible string 225 is configured to break in response to application of force to an elongated wire 235, described below, during retraction of the filter 210 to thereby permit recapture of the filter 210 in a catheter. For example, this arrangement may thereby permit the anchors 215 to advance out of the plurality of slits 221 thereby de-coupling the filter 210 from the woven stent 205. In addition, the bio-compatible string 225 is fixedly coupled to at least one of the plurality of anchors 215. In operation, this fixed coupling prevents the bio-compatible string 225 from breaking free from the apparatus 200 to avoid obstruction of blood flow.

Figure 15:
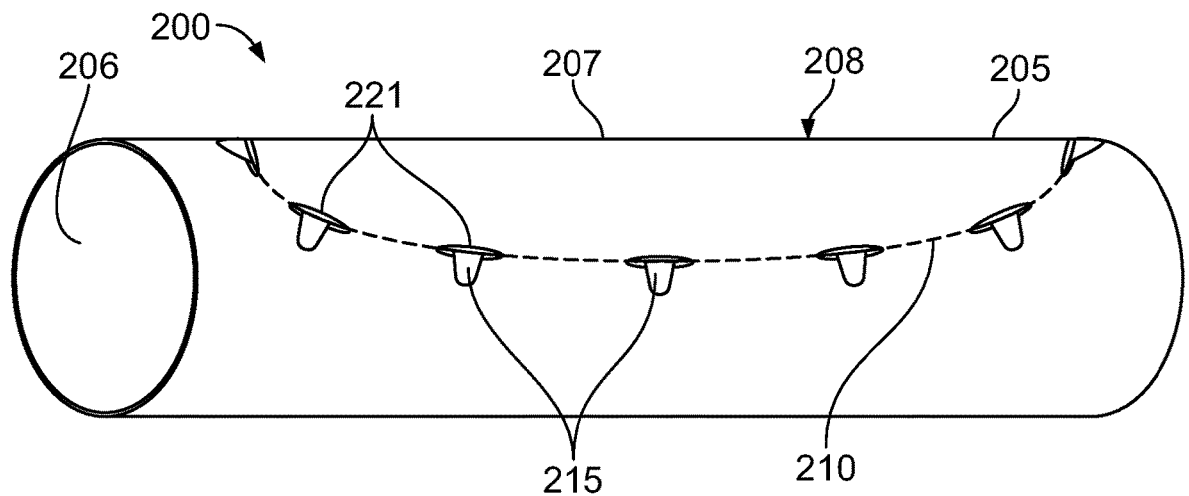
FIG. 15 is a diagrammatic representation of a side view of an apparatus, according to one example implementation, after the woven stent and the filter are coupled together.

In another example, shown in FIGS. 14-15, the plurality of anchors 215 have shape memory biased towards a closed condition such that the plurality of anchors 215 collapse against an exterior 208 of the woven stent 205 in both the compressed state and the expanded state and the plurality of anchors 215 are configured to be flexed to an open condition perpendicular to the filter 210 to be retracted out of the plurality of slits 221. For example, the plurality of anchors 215 may be wrapped with a band 230 that extends around the periphery 211 of the filter 210 prior to advancing the anchors 215 through the plurality of slits 221. The band 230 has a height shorter than the plurality of anchors 215 to permit clearance to advance through the slits 221, and the band 230 forces the plurality of anchors 215 to extend longitudinally from a face of the filter 210 in the open condition. Then, the hand 230 de-couples from the plurality of anchors 215 thereby permitting the anchors 215 to return to the closed position and to mate the filter 210 against an interior surface 206 of sidewall 207 of the woven stent 205. The band 230 may be de-coupled by severing the band 230, for example. In this embodiment, the plurality of anchors 215 in the closed condition are arranged flat against the exterior 208 of the woven stent 205 such that the anchors 215 are perpendicular to or in opposition to the slits 221.

Figure 16:
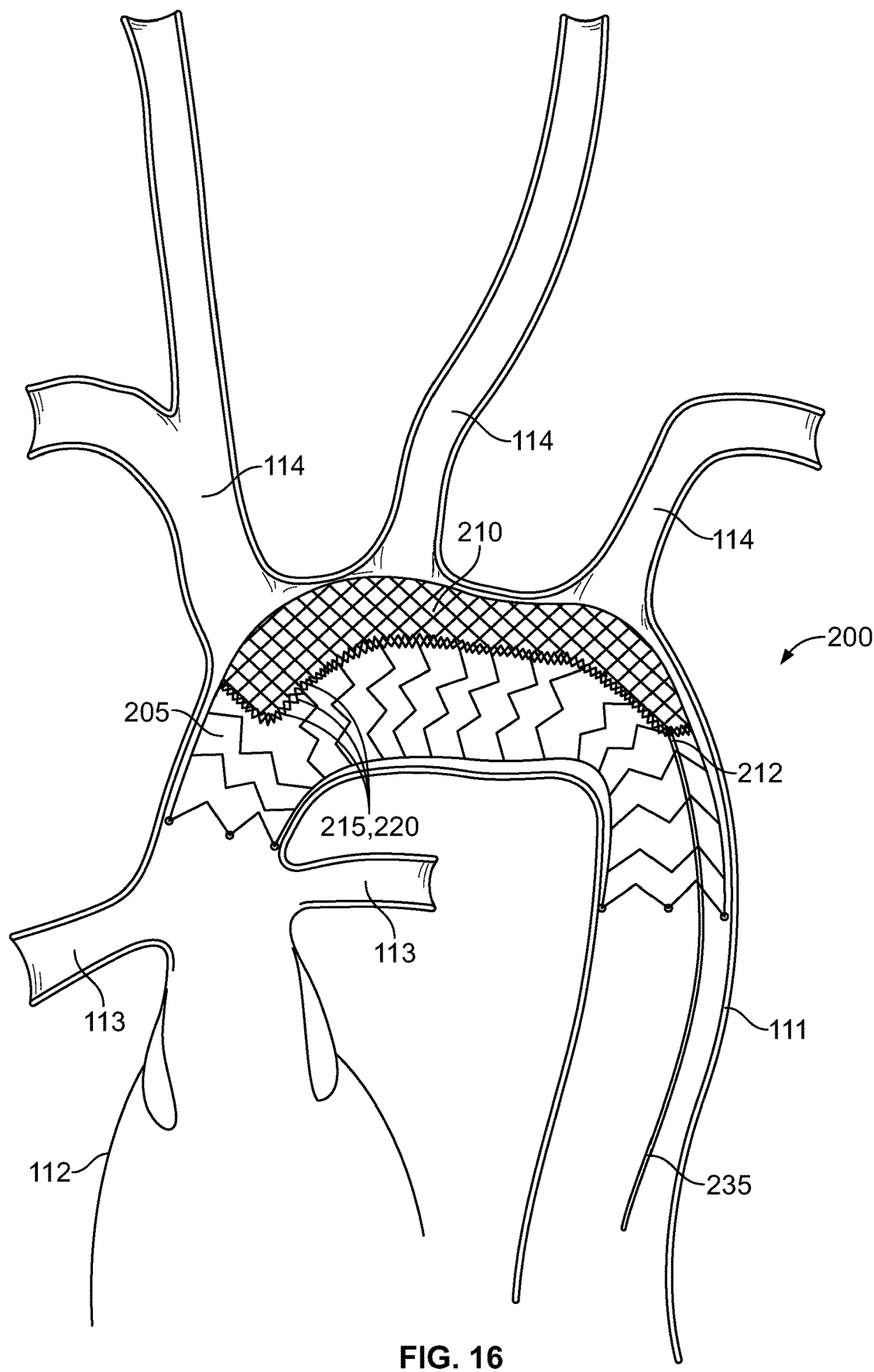
FIG. 16 is a diagrammatic representation of a side view of an apparatus, according to one example implementation.

In an alternative example, as shown in FIG. 16, the plurality of anchors 215 have a higher resistance to electric current than the plurality of attachment points 220 such that the filter 210 may be decoupled from the woven stent 205 via electrolytic detachment. For example, the filter 210 may be coupled to the woven stent 205 via attachment points that have a higher resistance to electric current than the structure of the woven stent 205 such that the application of current to the filter 210 or woven stent 205 results in release of the filter 210 from the woven stent 205.

The filter 210 includes an elongated wire 235 coupled to a second end 212 of the filter 210 and configured to permit the filter to de-couple from the woven stent 205 and retract into a catheter. The elongated wire 235 may be 0.014" or 0.018" wire that is coupled externally or internally to be snared if later retrieval is desired. If the elongated wire 235 is arranged internally within the woven stent 205, the elongated wire 235 may include a "snarable" tab.

The filter 210 of the second aspect of the disclosure may be used with any embodiments of the apparatus 100 according to the first aspect of the disclosure.

Figure 17:
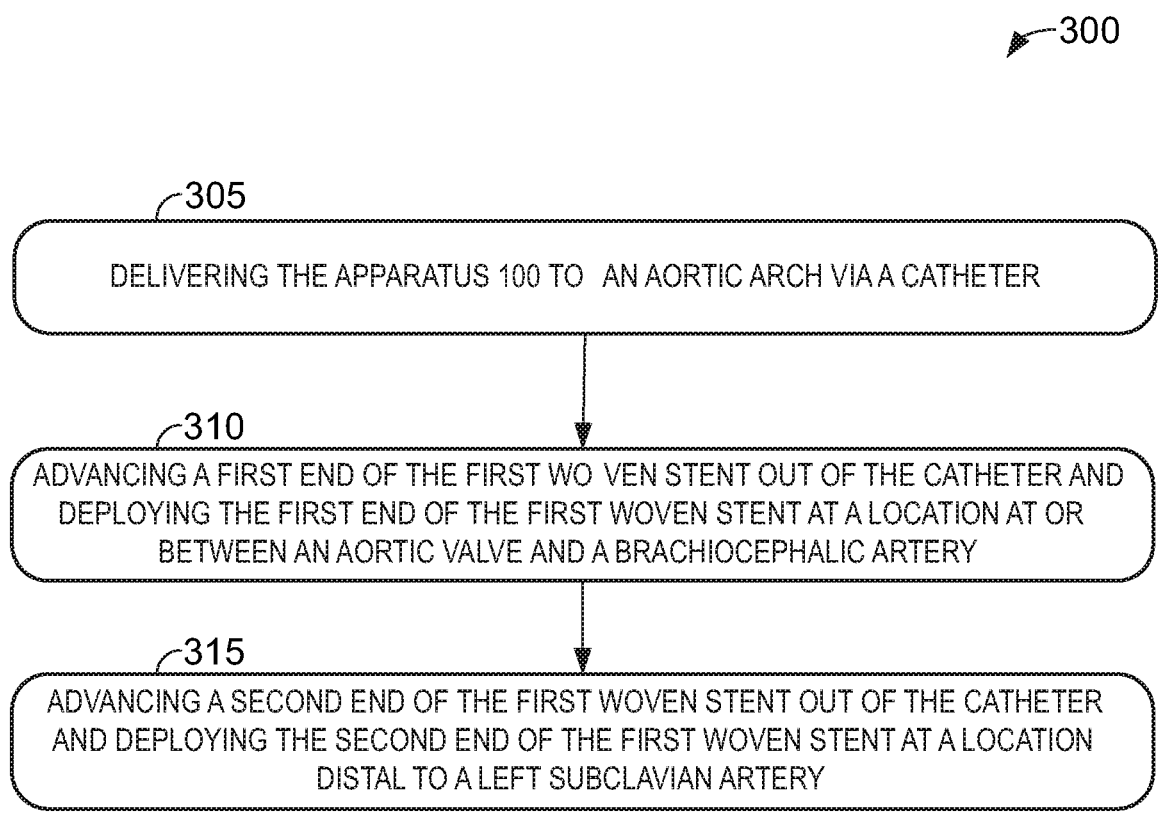
FIG. 17 shows a flowchart of a method, according to an example implementation.

In a third aspect, a method 300 is provided to treat a patient suffering from a compromised aorta. For example, the method 300 may be used to treat a dilated or dissected ascending aorta, EDS, and/or MFS with an enlarged aorta, including an aneurysmal sac in the aortic arch. Referring now to FIG. 17, a method 300 is illustrated using the apparatus 100 according to the first aspect of the disclosure. Method 300 includes, at block 305, delivering the apparatus 100, according to the first aspect, to an aortic arch via a catheter. Next, at block 310, a first end 106 of the first woven stent 105 is advanced out of the catheter 102 and the first end 106 of the first woven stent 105 is deployed at a location at or between the aortic valve and the brachiocephalic artery. Then, at block 315, a second end 107 of the first woven stent 105 is advanced out of the catheter 102 and the second end 107 of the first woven stent 105 is deployed at a location distal to the left subclavian artery. In various embodiments, the second end 107 of the first woven stent 105 may be deployed at or near the branch into the common iliac arteries.

In one optional example, the method 300 further includes penetrating the first woven stent 105 with at least one of a catheter or a guidewire 103 thereby causing a punctured portion 166 of the first woven stent 105 to roll backwards forming a cuff around the catheter or the guidewire 103. Next, the catheter or the guidewire 103 is advanced into one of the Great vessels 114. Then, a first end of an extension stent 167 or an extension stent graft is deployed into one of the Great vessels 114, and a second end of the extension stent or the extension stent graft is deployed into the first woven stent 105 through the cuff.

In one optional example, the method 300 further includes advancing at least one of a catheter, guidewire, or expandable balloon through at least one of the plurality of openings 141 in the flow window 140 and into a coronary artery 113. The at least one of the plurality of openings 141 in the flow window 140 are permanently deformed and enlarged via the catheter, guidewire or expandable balloon. These steps have the technical effect of increasing blood flow to the coronary arteries 113.

In an alternative optional example, the method 300 includes advancing a guidewire through one of a plurality of openings 141 of the flow window 140 and into one of the coronary arteries 113. Then, an intermediate catheter 196 is advanced over the guide wire into one of the coronary arteries 113. Next, the intermediate catheter 196 is retracted from a second end 177 of the second woven stent 175 thereby permitting the second end 177 to expand into the one of the coronary arteries. And the intermediate catheter is further retracted exposing and permitting expansion of the first retention disk 180 and second retention disk 185 on opposing sides of the flow window 141.

In another optional example, the method 300 further includes aligning the weave pattern 120 arranged along the outer curvature 121 of the woven stent 105 with the Great vessels 114. The technical effect of this step is to permit access to the Great vessels 114 for a catheter, guidewire, or expandable balloon.

In one optional example, the method 300 may further involve deploying the anchoring stent 135 at a sinotubular juncture 112. The technical effect of this step is to permit healthy tissue-to-healthy tissue anchoring for treatment of segments of the aorta 111.

In an optional example, the method 300 may further involve deploying a prosthetic valve 136 in an aortic valve. This may be beneficial in treating a hostile arch ("atheroma").

In another optional example, the method 300 includes the first woven stent 105 packed to adjust a density of cells formed by the weave pattern 120 arranged along the outer curvature 121 of the first woven stent 105. Packing the stent refers to the act of pushing the stent into a target lumen 110 in which the stent is being deployed such that the stent has a length shorter than the original unconstrained length.

In another optional example, the method 300 further includes deploying the apparatus according to any of the apparatus 100, 200 in a distal end of a previously deployed prosthetic valve in the aortic arch. This may be beneficial in treating a hostile arch with atheroma, ascending aortic aneurysm, or Stanford type A dissection.

In one optional example, the method 300 may further involve aligning the flow window 140 with coronary arteries 113. This may result in increased blood flow to the coronary arteries 113.

Figure 18:
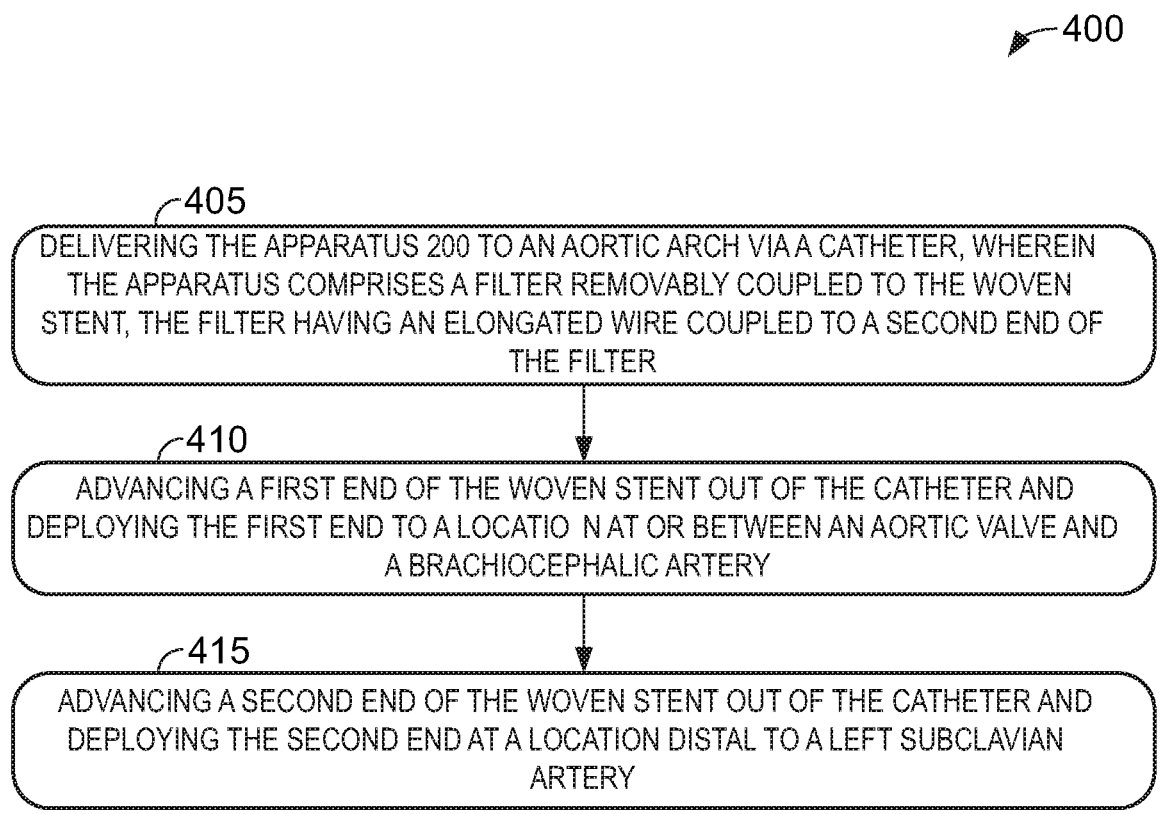
FIG. 18 shows a flowchart of a method, according to an example implementation.

In a fourth aspect of the disclosure, a method 400 is provided to treat a patient suffering from a compromised aorta 111. For example, the method may be used to treat a dilated or dissected ascending aorta, EDS, and/or MFS with an enlarged aorta, including an aneurysmal sac in the aortic arch. Referring now to FIG. 18, a method 400 is illustrated using the apparatus according to the second aspect of the disclosure. Method 400 includes, at block 405, delivering the apparatus 200 according to the second aspect of the disclosure to an aortic arch via a catheter. In this example, the apparatus 200 includes a filter 210 removably coupled to the woven stent 205, and the filter 210 having an elongated wire 235 coupled to a second end 212 of the filter 210. Then, at block 410, the first end 206 of the woven stent is advanced out of the catheter and the first end of the woven stent is deployed at a location at or between an aortic valve and a brachiocephalic artery. Next, at block 415, a second end of the woven stent 205 is advanced out of the catheter and the second end of the woven stent 205 is deployed at a location distal to a left subclavian artery.

In one optional example, the method includes advancing a recapture catheter along the elongated wire 235 of the filter. Then, a force is applied to the elongated wire 235 thereby causing the filter 210 to de-couple from the woven stent graft 205. Next, the filter 210 is pulled into the recapture catheter. And the recapture catheter and the filter 210 are retracted from the aortic arch.

In another optional example, the plurality of attachment points 220 of the woven stent 205 include a plurality of slits 221 through a sidewall 207 of the woven stent 205. The plurality of anchors 215 have shape memory biased towards a closed condition such that the plurality of anchors 215 collapse against an exterior 208 of the woven stent 205 in both the compressed state and the expanded state and the plurality of anchors 215 are configured to be flexed to an open condition perpendicular to the filter 210 to be retracted out of the plurality of slits 221. In this example, the method 400 includes flexing the plurality of anchors 215 from the closed condition to the open condition via the force applied to the elongated wire 235 of the filter 210 thereby permitting the plurality of anchors 215 to be retracted through the plurality of slits 221 of the woven stent 205.

In another optional example, the plurality of attachment points 220 of the woven stent 205 include a plurality of slits 221 through a sidewall 207 of the woven stent 205. A plurality of openings 216 are defined in the plurality of anchors 215. And the apparatus 200 includes a bio-compatible string 225 disposed through the plurality of openings 216 defined in the plurality of anchors 215. In this example, the method 400 includes breaking the bio-compatible string via the force applied to the elongated wire 235 of the filter 210 thereby permitting the plurality of anchors 215 to be retracted through the plurality of slits 221 of the woven stent 205.

In one optional example, before delivering the apparatus 200 according to the second aspect of the disclosure to the aortic arch via the catheter, the woven stent is coupled to the filter 210 by aligning a plurality of anchors 215 of the filter with a plurality of slits 221 of the woven stent 205. Then, the anchors 215 are advanced through the plurality of slits 221. In a further example, after advancing the plurality of anchors 215 through the plurality of slits 221, a biocompatible string 225 is threaded through the plurality of openings 216 of the anchors 215 about the periphery 211 of the filter 210. Then, the bio-compatible string 225 is fixedly coupled to at least one of the plurality of anchors 215. These steps may be conducted when the woven stent 205 and the filter 210 are in a pre-deployment state.

In an alternative optional example, the plurality of anchors 215 have shape memory biased towards a closed condition and the plurality of anchors 215 are configured to be flexed to an open condition. In this example, the method 400 includes wrapping the plurality of anchors 215 with a band 230 that extends around the periphery 211 of the filter 210 prior to advancing the anchors 215 through the plurality of slits 221. The band 230 has a height shorter than the plurality of anchors 215, and the band 230 forces the plurality of anchors 215 to extend longitudinally from a face of the filter 210 in the open condition. Then, the band 230 de-couples from the plurality of anchors 215 thereby permitting the anchors 215 to return to the closed position and to mate the filter 210 against an interior surface 206 of the sidewall 207 of the woven stent 205. The band 230 may be de-coupled by severing the band 230, for example. In this example, the plurality of anchors 215 are configured to collapse against an exterior 208 of the woven stent 205 in the expanded deployed state when pressed against a target lumen 110. In an alternative embodiment, the plurality of anchors have shape memory biased towards a closed condition and the plurality of anchors 215 are configured to be flexed to an open condition to be advanced through the plurality of slits 221. For example, the anchors 215 may be wrapped with a band 230, for example, that extends around the periphery 211 of the filter 210 and that has a height shorter than the anchors 215. In operation, the band 230 forces the anchors 215 to extend longitudinally from a face of the filter 210 in the open condition such that the ends of the anchors 215 may be advanced through the slits 221 and the band 230 may be de-coupled from the anchors 215 permitting the anchors 215 to return to the closed position and to mate the filter 210 with the interior surface 206 of the sidewall 207 of the woven stent 205.

In yet another example, the plurality of anchors 215 have a higher resistance to electric current than the plurality of attachment points 220. In this example, the method 400 includes applying electric current to the attachment points via the filter 210 and an elongated wire 235 thereby electrolytically de-coupling the filter 210 from the woven stent 205.

The description of different advantageous arrangements and methods have been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

The invention claimed is:

1. An apparatus, comprising:
   a first woven stent having a curved form in an expanded state, wherein, in the expanded state, at least a first portion of the first woven stent has a weave pattern arranged along an outer curvature of the first woven stent that is different than a weave pattern arranged along an inner curvature of the first woven stent, wherein the first woven stent is biased toward the curved form due to shape memory;
   an anchoring stent or a prosthetic valve coupled to a first end of the first woven stent such that there is a flow window having a plurality of openings arranged therebetween to permit blood flow through the plurality of openings; and
   a second woven stent configured to transition between a compressed state and an expanded state, wherein, in the compressed state, the second woven stent has an elongate tubular form and, in the expanded state, the second woven stent forms a first retention disk and a second retention disk arranged in series at a first end and a tubular form at a second end such that a lumen is defined between the first end and the second end of the second woven stent, wherein the second woven stent is configured to be disposed through one of the plurality of openings of the flow window in the expanded state and arranged such that (i) a portion of the first end of the first woven stent, (ii) a radial stent structure or (iii) two radial spaced-apart supports of the flow window are arranged between the first retention disk and the second retention disk and the second end of the second woven stent is configured to be disposed within a coronary artery, wherein the second woven stent further comprises a plurality of detachment tabs configured to be removably coupled to a catheter in the compressed state, wherein the plurality of detachment tabs have shape memory and are configured to lie flat against the first end of the second woven stent in the expanded state.

2. The apparatus of claim 1, wherein the first woven stent is configured to act as a flow diverter.

3. The apparatus of claim 1, wherein, in the expanded state, the first end of the first woven stent tapers outwardly in the form of a flange.

4. The apparatus of claim 1, wherein the plurality of openings of the flow window are defined in a second portion of the first woven stent arranged at the first end of the first woven stent, wherein a pick density of the second portion of the first woven stent is lower than a pick density of the first portion of the first woven stent.

5. The apparatus of claim 4, wherein the pick density of the first portion of the first woven stent has a pore size ranging from 0.005 mm$^2$ to 1.0 mm$^2$ in the expanded state.

6. The apparatus of claim 4, wherein the pick density of the second portion of the first woven stent has a pore size ranging from 0.01 mm$^2$ to 1.0 mm$^2$ in the expanded state.

7. The apparatus of claim 1, wherein the flow window comprises a radial stent formed from a sinusoidal-shaped wire or a plurality of radially spaced-apart supports that couples the anchoring stent or the prosthetic valve to the first woven stent, wherein the plurality of openings of the flow window are defined between sinusoidal components of the radial stent or the plurality of radially spaced-apart supports.

8. The apparatus of claim 7, wherein the flow window has a length ranging from 4 mm to 20 mm in the expanded state.

9. The apparatus of claim 1, wherein a diameter of the first woven stent ranges from about 5 mm to about 60 mm in the expanded state, and wherein a length of the first woven stent ranges from about 10 mm to about 1000 mm in the expanded state.

10. The apparatus of claim 1, wherein the first woven stent is configured to be penetrated by a guidewire or catheter and thereby cause a punctured portion of the first woven stent to roll backwards forming a cuff around the catheter or the guidewire.

11. The apparatus of claim 1, wherein the plurality of openings of the flow window are configured to be expanded and deformed upon application of force from at least one of an expandable balloon, a catheter or a guidewire.

12. The apparatus of claim 1, wherein the weave pattern arranged along the outer curvature of the first woven stent is configured to prevent the passage therethrough of particles having a diameter of 20 µm or greater.

13. The apparatus of claim 1, further comprising Gore-Tex, felt, gel-foam or combinations thereof coupled to the exterior of the second woven stent between the first retention disk and the second retention disk.

14. A method comprising:
  delivering the apparatus according to claim 1 to an aortic arch via a catheter;
  advancing the first end of the first woven stent out of the catheter and deploying the first end of the first woven stent at a location at or between an aortic valve and a brachiocephalic artery; and
  advancing a second end of the first woven stent out of the catheter and deploying the second end of the first woven stent at a location distal to a left subclavian artery.

15. The method of claim 14, further comprising:
  penetrating the first woven stent with at least one of a catheter or a guidewire thereby causing a punctured portion of the first woven stent to roll backwards forming a cuff around the catheter or the guidewire;
  advancing the catheter or the guidewire into one of the Great vessels;
  deploying a first end of an extension stent or an extension stent graft into one of the Great vessels; and
  deploying a second end of the extension stent or the extension stent graft into the first woven stent through the cuff.

16. The method of claim 14, further comprising:
  advancing at least one of a catheter, guidewire, or expandable balloon through at least one of the plurality of openings in the flow window and into a coronary artery; and
  permanently deforming and enlarging the at least one of the plurality of openings in the flow window via the catheter, guidewire or expandable balloon.

17. The method of claim 14, further comprising:
  aligning the weave pattern arranged along the outer curvature of the first woven stent with the Great vessels.

* * * * *